(12) United States Patent
Rhoades et al.

(10) Patent No.: US 11,197,943 B1
(45) Date of Patent: Dec. 14, 2021

(54) FAN FOR IMPROVING AIR QUALITY

(71) Applicant: DELTA T, LLC, Lexington, KY (US)

(72) Inventors: Lennie Rhoades, Nicholasville, KY (US); Eric Evans, Lexington, KY (US); Jay Fizer, Lexington, KY (US); Marc McKinzie, Lexington, KY (US); Pete Maley, Lexington, KY (US); Mike Smith, Lexington, KY (US); Jayme Webb, Lexington, KY (US)

(73) Assignee: DELTA T, LLC, Lexington, KY (US)

( * ) Notice: Subject to any disclaimer, the term of this patent is extended or adjusted under 35 U.S.C. 154(b) by 0 days.

(21) Appl. No.: 17/228,938

(22) Filed: Apr. 13, 2021

Related U.S. Application Data

(63) Continuation of application No. 17/147,086, filed on Jan. 12, 2021, now Pat. No. 11,027,038.

(60) Provisional application No. 63/060,826, filed on Aug. 4, 2020, provisional application No. 63/045,882, filed on Jun. 30, 2020, provisional application No. 63/038,446, filed on Jun. 12, 2020, provisional application No. 63/029,105, filed on May 22, 2020.

(51) Int. Cl.
| | |
|---|---|
| *A61L 9/22* | (2006.01) |
| *F04D 13/06* | (2006.01) |
| *F04D 25/08* | (2006.01) |
| *F04D 29/32* | (2006.01) |

(52) U.S. Cl.
CPC ............. *A61L 9/22* (2013.01); *F04D 13/06* (2013.01); *F04D 25/088* (2013.01); *F04D 29/325* (2013.01); *A61L 2209/134* (2013.01)

(58) Field of Classification Search
CPC ...... F04D 13/06; F04D 25/088; F04D 29/325; F04D 29/701; F04D 29/703; A61L 9/22; A61L 2209/134
See application file for complete search history.

(56) References Cited

U.S. PATENT DOCUMENTS

| | | | |
|---|---|---|---|
| 4,422,824 A | 12/1983 | Eisenhardt, Jr. | |
| 4,597,781 A * | 7/1986 | Spector | B03C 3/011 96/52 |
| 5,082,422 A | 1/1992 | Wang | |
| 5,151,011 A | 9/1992 | Rezek | |
| 5,795,131 A | 8/1998 | Crowhurst et al. | |
| 6,036,331 A * | 3/2000 | Acquisto | F04D 29/005 362/96 |
| 6,120,262 A | 9/2000 | McDonough et al. | |
| 6,160,956 A | 12/2000 | Pelonis | |
| 6,244,820 B1 | 6/2001 | Yilmaz | |
| 6,461,032 B2 | 10/2002 | McKinley | |
| 7,252,478 B2 | 8/2007 | Aynsley | |

(Continued)

*Primary Examiner* — Patrick Hamo
(74) *Attorney, Agent, or Firm* — Dickinson Wright PLLC; Andrew D. Dorisio (57) ABSTRACT

A fan is for improving air quality, such as in an indoor environment. The fan includes a motor and a rotatable hub coupled to the motor. At least one fan blade includes a first end portion coupled to the rotatable hub and a second end portion radially distant from the rotatable hub. At least one ion generator is carried by the second end portion of the at least one fan blade, such as by a winglet associated therewith. A stationary tube passes through the rotatable hub including a conduit for transmitting power. A rotary coupling is also provided for transmitting power from the conduit to the at least one ion generator.

22 Claims, 11 Drawing Sheets

(56) References Cited

U.S. PATENT DOCUMENTS

| | | |
|---|---|---|
| 7,763,212 B2 | 7/2010 | McEllen |
| 7,879,299 B2 | 2/2011 | McEllen |
| 8,080,203 B2 | 12/2011 | First et al. |
| 8,080,819 B2 | 12/2011 | Mueller et al. |
| 8,207,821 B2 | 6/2012 | Roberge et al. |
| 9,393,338 B2 | 7/2016 | Livchak et al. |
| 9,399,998 B1 * | 7/2016 | Hardie ................ F04D 25/088 |
| 9,707,310 B2 | 7/2017 | Watanabe et al. |
| 10,125,971 B2 | 11/2018 | Graziano et al. |
| 10,207,019 B2 | 2/2019 | Takasahara et al. |
| 10,498,099 B2 | 12/2019 | Walker et al. |
| 10,502,407 B1 | 12/2019 | Spiro |
| 10,808,964 B2 | 10/2020 | Polidoro |
| 10,897,806 B1 | 1/2021 | Bucher et al. |
| 10,987,440 B1 | 4/2021 | Sood et al. |
| 11,027,038 B1 | 6/2021 | Rhoades et al. |
| 11,060,712 B2 | 7/2021 | Niemiec et al. |
| 2005/0058584 A1 | 3/2005 | Shyu |
| 2009/0097975 A1 * | 4/2009 | Aynsley ................ F04D 29/601 416/32 |
| 2009/0122572 A1 | 5/2009 | Page et al. |
| 2009/0129974 A1 | 5/2009 | McEllen |
| 2011/0103982 A1 | 5/2011 | A. et al. |
| 2012/0199005 A1 | 8/2012 | Koji et al. |
| 2013/0272879 A1 | 10/2013 | Chen |
| 2015/0009666 A1 | 1/2015 | Keng et al. |
| 2015/0110625 A1 | 4/2015 | De Siqueira Indio Da Costa et al. |
| 2017/0248148 A1 | 8/2017 | Kohen |
| 2019/0264702 A1 | 8/2019 | Huggins et al. |
| 2019/0345946 A1 | 11/2019 | Register et al. |
| 2020/0197550 A1 | 6/2020 | Barron et al. |
| 2020/0332969 A1 | 10/2020 | Soler et al. |
| 2020/0340487 A1 | 10/2020 | Register et al. |
| 2020/0366125 A1 | 11/2020 | Chen |
| 2021/0016216 A1 | 1/2021 | Popa-Simil et al. |

* cited by examiner

FAN FOR IMPROVING AIR QUALITY

This patent application is a continuation of U.S. application Ser. No. 17/147,086, filed on Jan. 12, 2021 which claims the benefit of U.S. Provisional Patent Application Nos. 63/060,826, 63/045,882, 63/038,446, and 63/029,105, the disclosures of which are incorporated herein by reference.

TECHNICAL FIELD

This application relates to the air circulation arts and, more particularly, to a fan adapted for improving air quality, such as by minimizing the presence of airborne germs or pathogens.

BACKGROUND

A variety of fan systems have been made and used over the years in a variety of contexts. For instance, various ceiling fans are disclosed in U.S. Pat. No. 7,284,960, entitled "Fan Blades," issued Oct. 23, 2007; U.S. Pat. No. 6,244,821, entitled "Low Speed Cooling Fan," issued Jun. 12, 2001; U.S. Pat. No. 6,939,108, entitled "Cooling Fan with Reinforced Blade," issued Sep. 6, 2005; and U.S. Pat. No. D607,988, entitled "Ceiling Fan," issued Jan. 12, 2010. The disclosures of each of those U.S. patents are incorporated by reference herein. Additional exemplary fans are disclosed in U.S. Pat. Pub. No. 2008/0008596, entitled "Fan Blades," published Jan. 10, 2008; U.S. Pat. Pub. No. 2009/0208333, entitled "Ceiling Fan System with Brushless Motor," published Aug. 20, 2009; and U.S. Pat. Pub. No. 2010/0278637, entitled "Ceiling Fan with Variable Blade Pitch and Variable Speed Control," published Nov. 4, 2010, the disclosures of which are also incorporated by reference herein. It should be understood that teachings herein may be incorporated into any of the fans described in any of the above-referenced patents, publications, or patent applications. It should also be understood that a fan may include sensors or other features that are used to control, at least in part, operation of a fan system. For instance, such fan systems are disclosed in U.S. Pat. Pub. No. 2009/0097975, entitled "Ceiling Fan with Concentric Stationary Tube and Power-Down Features," published Apr. 16, 2009, the disclosure of which is incorporated by reference herein; U.S. Pat. Pub. No. 2009/0162197, entitled "Automatic Control System and Method to Minimize Oscillation in Ceiling Fans," published Jun. 25, 2009, the disclosure of which is incorporated by reference herein; and U.S. Pat. Pub. No. 2010/0291858, entitled "Automatic Control System for Ceiling Fan Based on Temperature Differentials," published Nov. 18, 2010, the disclosure of which is incorporated by reference herein. Alternatively, any other suitable control systems/features may be used in conjunction with embodiments described herein.

In some environments, it is desirable to eliminate airborne diseases and disease vectors from the air. Existing methods for reducing airborne disease transmission between room occupants include fresh air ventilation, filtration, and direct deactivation/destruction methods such as irradiation or oxidation of the pathogens themselves. For instance, this can be achieved through the use of an air ionizer or ion generator, which is a device that uses high voltage energy to ionize (electrically charge) air molecules. Airborne particles become charged as they attract charged ions from the ionizer by electrostatic attraction. The particles in turn are then attracted to any nearby earthed (grounded) conductors, such as plates within an air cleaner, or simply the nearest walls and ceilings, and disabled as a result.

As can be appreciated, any germicidal fixture positioned in a space is somewhat effective, but obviously limited in efficacy per se given its stationary nature (and the use of multiple stationary devices may be considered costly and inefficient in most applications). In many applications, such stationary devices do not receive enough airflow as a result of circulation because a typical fan is designed for force air toward the floor, and not necessarily to any generators of germicidal energy (which would typically be mounted on the ceiling or walls). Furthermore, many of past approaches are not implemented successfully due to lack of operator training, maintenance issues, sub-par user interfaces and experiences, and cost.

Accordingly, a need is identified for an improved manner of providing a fan with a germicidal capability. In particular, the fan would for part of a system providing a degree of automation of operating certain sterilizing functions that avoids the problems associated with the above-mentioned approaches. Additional aspects of germicidal fans are also disclosed.

SUMMARY

According to a first aspect of the disclosure, a fan for improving air quality is provided. The fan includes a motor, a rotatable hub coupled to the motor, and at least one fan blade comprising a first end coupled to the rotatable hub, a second end radially distant from the rotatable hub, and a winglet attached to the second end. At least one ion generator is carried by the winglet.

In one embodiment, the at least one ion generator is mounted to an inner face of the winglet. The at least one ion generator may be mounted to the winglet below a plane of the at least one fan blade. A rotary coupling may be provided for transmitting power to the at least one ion generator.

A stationary tube passing through the hub may be provided for conveying power to the at least one ion generator, the rotary coupling being connected to the stationary tube. A conduit for supplying power for the ion generator passes from the hub, along the at least one fan blade, and to the winglet to connect to the at least one ion generator. The at least one blade may include a passage extending from the first end to the second end, the passage including wires for transmitting power to the at least one ion generator through the winglet.

The fan may include a plurality of fan blades coupled to the rotatable hub, each having a winglet including an ion generator. The at least one fan blade has a length of greater than about six feet.

According to a further aspect of the disclosure, a fan is provided for improving air quality. The fan includes a motor, a rotatable hub coupled to the motor, and at least one fan blade comprising a first end coupled to the rotatable hub and a second end radially distant from the rotatable hub. The fan further includes at least one ion generator carried by the fan blade at a second end thereof.

In one embodiment, the fan further includes a winglet at the second end of the fan blade for carrying the at least one ion generator. The ion generator may be mounted to an inner face of the winglet, or below a plane of the at least one fan blade. A rotary coupling is provided for transmitting power to the at least one ion generator. A stationary tube passes through the hub for conveying power to the at least one ion generator, the rotary coupling being connected to the stationary tube. A conduit is provided for supplying power for the ion generator, which conduit passes from the hub, along the at least one fan blade, and to the at least one ion generator. The at least one blade includes a passage extending from the first end to the second end, the passage including wires for transmitting power to the at least one ion generator through the winglet.

According to a further aspect of the disclosure, a fan for improving air quality is provided. The fan comprises a motor, a rotatable hub coupled to the motor, and at least one fan blade including a first end coupled to the rotatable hub and a second end radially distant from the rotatable hub. At least one generator for generating germicidal energy is also provided. A stationary tube passes through the rotatable hub including a conduit for transmitting power, and a rotary coupling is provided for transmitting power from the conduit to the at least one ion generator.

Still a further aspect of the disclosure relates to a fan for improving air quality. The fan includes a motor, a rotatable hub coupled to the motor, and at least one fan blade comprising: i. a first end portion coupled to the rotatable hub, ii. a second end portion radially distant from the rotatable hub. At least one ion generator is carried by and located external of the fan blade, such as at the second end portion of the fan blade.

BRIEF DESCRIPTION OF THE DRAWING FIGURES

While the specification concludes with claims which particularly point out and distinctly claim the invention, it is believed the aspects of the disclosure will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
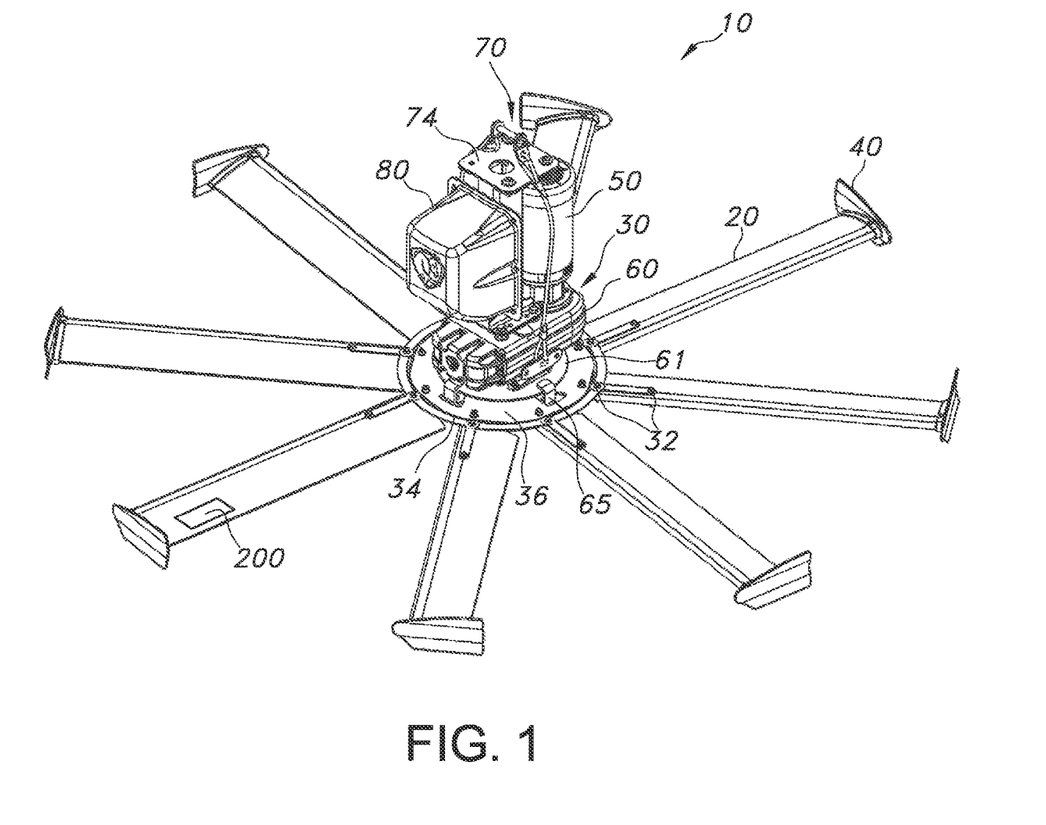
FIG. 1 depicts a perspective view an exemplary fan.

FIG. 1 shows a merely exemplary fan 10. Fan 10 of this example comprises fan blades 20 and a rotating hub 30. Winglets 40 are secured to the outer end 22 of each fan blade 20, and thus form a portion thereof, and establish an end surface or cap to the fan blade 20, which are noted below is typically hollow and formed of a continuous piece of material. In this example, fan 10 also includes a motor 50 and a gearbox 60 that rotationally drive hub 30, a mounting member 70 by which fan 10 may be mounted to a ceiling or other structure; and a control box 80.

Fan blades 20 of the present example are substantially hollow and are formed of extruded aluminum having an airfoil shaped cross-section with a solid body, including a solid leading edge and solid trailing edge, which may be formed of extruded aluminum, though any other suitable configurations, manufacturing techniques, and/or material(s) may be used. By way of example only, fan blades 20 may be configured in accordance with any of the teachings in U.S. Pat. No. 7,284,960, entitled "Fan Blades," issued Oct. 23, 2007, the disclosure of which is incorporated by reference herein. Alternatively, fan blades (20) may be configured in accordance with any of the teachings in U.S. Pub. No. 2008/0008596, entitled "Fan Blades," published Jan. 10, 2008, the disclosure of which is incorporated by reference herein. In other versions, fan blades 20 are configured in accordance with any of the teachings in U.S. Pat. No. 6,244,821, entitled "Low Speed Cooling Fan," issued Jun. 12, 2001, the disclosure of which is incorporated by reference herein. In still other versions, fan blades (20) are configured in accordance with any of the teachings in U.S. Pat. No. 6,939,108, entitled "Cooling Fan with Reinforced Blade," issued Sep. 6, 2005, the disclosure of which is incorporated by reference herein.

Fan blades 20 may define a diameter of fan 10 of approximately 6 feet, approximately 8 feet, approximately 12 feet, or approximately 24 feet. Alternatively, fan 10 may have any other suitable diameter defined by fan blades 20. Furthermore, other suitable configurations for fan blades 20 will be apparent to those of ordinary skill in the art in view of the teachings herein.

Hub 30 of the present example comprises a plurality of mounting members (see element 30a in FIG. 2), which radiate outwardly from hub 30. Each mounting member is inserted into a respective fan blade 20, and the two are secured together with a pair of fasteners 32. Suitable configurations for a hub and methods for attaching a fan blade to a hub are disclosed in U.S. Pat. No. 7,284,960, entitled "Fan Blades," issued Oct. 23, 2007, the disclosure of which is incorporated by reference herein. Of course, any other suitable components, features, devices, or techniques may be used to secure fan blades 20 to hub 30.

Figure 2:
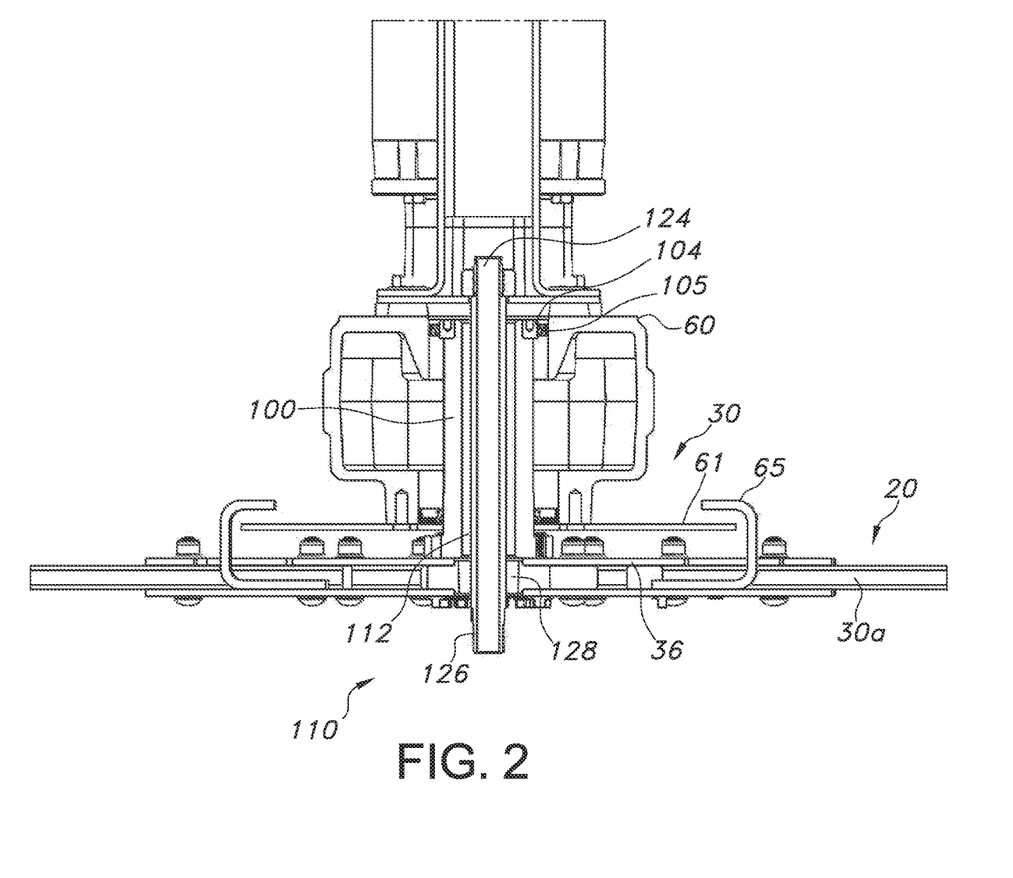
FIG. 2 depicts a partial perspective cross-sectional view of the drive assembly of the fan system of FIG. 1.

Hub 30 is secured to a hub mounting flange 36 by a plurality of fasteners (not shown), though any other suitable components, features, devices, or techniques may be used to secure hub 30 to hub mounting flange 36. Hub 30 thus rotates unitarily with hub mounting flange 36. Hub mounting flange 36 is secured to output shaft 100 by a plurality of fasteners 38. Hub mounting flange 36 (and, therefore, hub 30) thus rotates unitarily with output shaft 100. Again, though, any other suitable components, features, devices, or techniques may be used to secure hub mounting flange 36 to output shaft 100. Furthermore, in some versions, hub mounting flange 36 is omitted, such that hub 30 is secured directly to output shaft 100. Other suitable components and configurations for providing rotation of hub 30 by an output shaft 100 will be apparent to those of ordinary skill in the art in view of the teachings herein.

Several retainers 34 are also secured to fan blades 20 in the present example. By way of example only, such retainers 34 may reduce the likelihood of a fan blade 20 flying off of hub 30 in the event that a hub mounting member breaks free from hub 30 or otherwise fails. However, as with other components described herein, retainers 34 are merely optional, and may be varied, substituted, supplemented, or omitted as desired.

Figure 3:
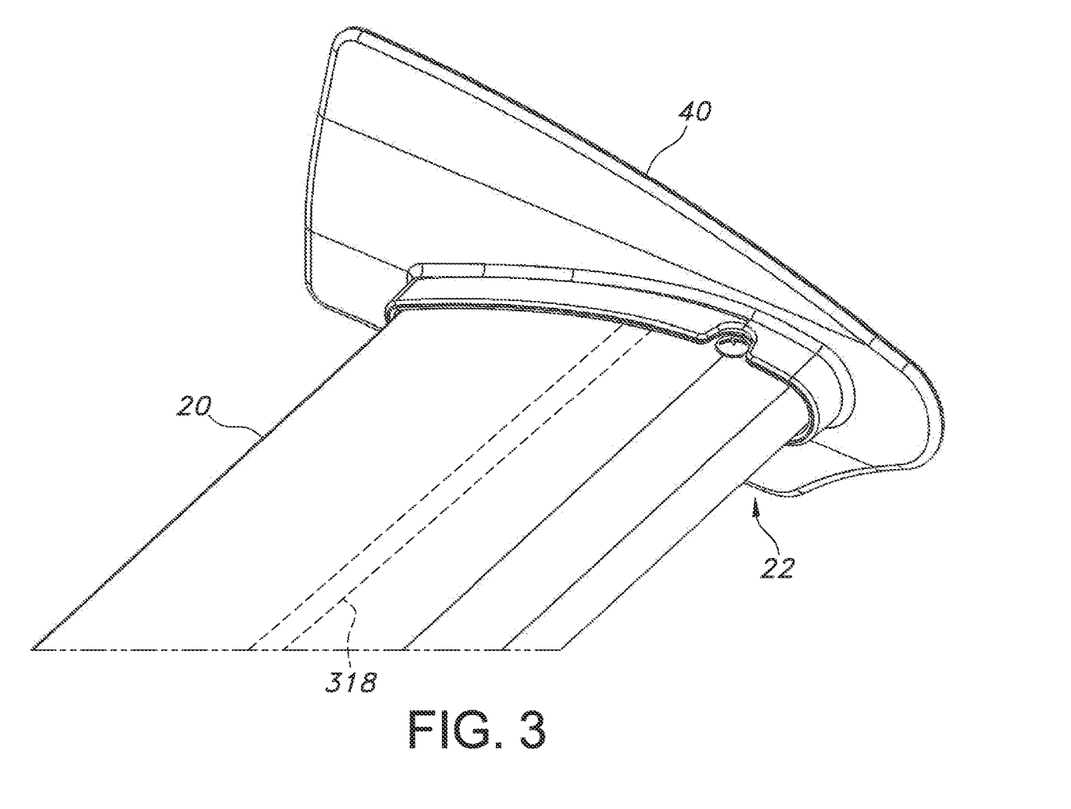
FIG. 3 is a partially cutaway view of a fan blade including a winglet.
Figure 4:
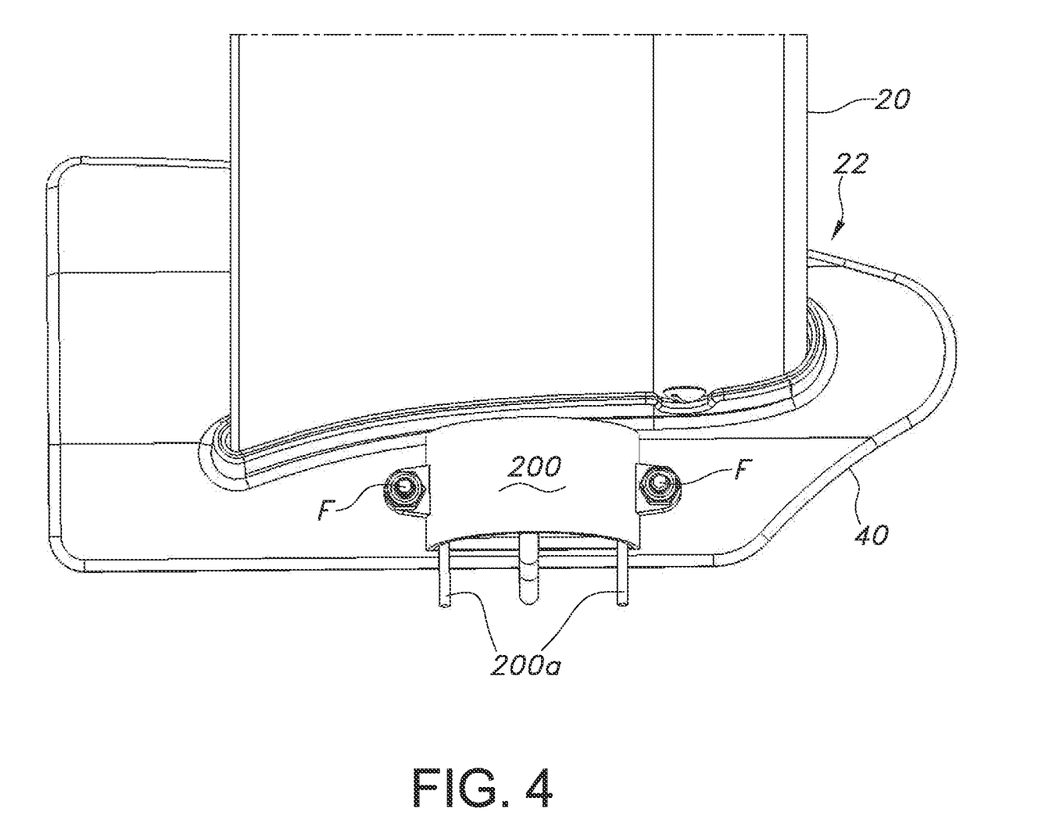
FIGS. 4 and 4A are partially cutaway views of a germicidal generator mounted to the winglet.

Winglets 40 may be configured in accordance with any of the teachings in U.S. Pat. No. 7,252,478, entitled "Fan Blade Modifications," issued Aug. 7, 2007, the disclosure of which is incorporated by reference herein. Alternatively, winglets 40 may be configured to include a cuff 40a, as shown in FIGS. 3-4, in accordance with any of the teachings in U.S. Pub. No. 2008/0014090, entitled "Cuffed Fan Blade Modifications," published Jan. 17, 2008, the disclosure of which is incorporated by reference herein. In other versions, winglets 40 are configured in accordance with any of the teachings in U.S. Pub. No. 2008/0213097, entitled "Angled Airfoil Extension for Fan Blade," published Sep. 4, 2008, the disclosure of which is incorporated by reference herein. Still other suitable configurations for winglets 40 will be apparent to those of ordinary skill in the art in view of the teachings herein.

Motor 50 may have an external stator (not shown) with windings; and a rotor without windings. The rotor may be coupled with the output shaft 100, which rotates unitarily with the rotor. Motor 50 of the present example may be configured to provide a maximum output power to gearbox 60 of approximately one to approximately two or approximately three horsepower (all inclusive); and a maximum output speed between approximately 1,750 RPM, inclusive, and approximately 3,500 RPM, inclusive. Alternatively, motor 50 may provide any other desired output power and/or output speed.

Motor 50 also includes a control interface, through which motor 50 receives commands from control box 80, as will be described in greater detail below. Motor 50 may also send data to control box 80 via control interface in some versions, including but not limited to data indicative of motor temperature, speed, etc., though such communications are not necessary in all versions. Communication through control interface may thus be unidirectional or bi-directional. It should be understood that motor 50 may be varied in any number of ways. By way of example only, motor 50 may have an internal stator and an external rotor, and may omit gearbox. Still other ways in which motor 50 may be varied will be apparent to those of ordinary skill in the art in view of the teachings herein.

If present, gearbox 60 of the present example may be a mechanical gearbox, and is configured to transfer rotary motion from motor 50 to the hollow output shaft 100 secured to hub mounting flange 36. In particular, gearbox 60 includes gears (not shown) that are in a parallel arrangement and are configured to provide a gear ratio of approximately 38:1 in the present example. Alternatively, any other suitable ratio may be used. In the present example, output shaft 100 is driven by a gear (not shown) that is coaxial with output shaft 100 and shrink/press fit to output shaft 100. Suitable structures and configurations for such gears and shafts will be apparent to those of ordinary skill in the art in view of the teachings herein, as will other suitable contents of and arrangements within a gearbox 60 (to the extent that a gearbox 60 is used at all).

In some versions, motor 50 and gearbox 60 are configured such that the maximum rotational speed of fan 10 is between approximately 125 RPM, inclusive, and approximately 250 RPM, inclusive. For instance, a maximum rotational speed of approximately 180 RPM may be used. In some other versions, a maximum rotational speed may be between approximately 50 RPM, inclusive, and approximately 100 RPM, inclusive. For instance, a maximum rotational speed of approximately 82 RPM may be used. In other versions, a maximum rotational speed may be between approximately 35 RPM, inclusive, and approximately 55 RPM. For instance, a maximum rotational speed of approximately 42 RPM may be used. Of course, any other suitable rotational speed may be used.

As shown in FIGS. 1-2, a plate 61 is secured to the bottom of the housing of gearbox 60. By way of example only, plate 61 may be formed of steel or any other suitable material or combination of materials. As shown in FIG. 1, several brackets 65 extend inwardly from hub 30. Brackets 65 are configured such that they extend over the top of plate 61 without contacting plate 61 during normal operation of fan 10. Brackets 65 may thus rotate with hub 30 without contacting the top of plate 61, such that the radially inwardmost portions of brackets 65 instead essentially "hover" over plate 61, as perhaps best understood from FIG. 2. Brackets 65 are further configured such that, in the event that hub 30 decouples from hub mounting flange 36, or in the event that hub mounting flange 36 decouples from output shaft 100, brackets will catch on plate 61 to prevent such components from falling completely free of the upper portions of fan 10. Plate 61 and brackets 65 may thus provide a safety measure in case of failure of fasteners or other components of fan 10. As with other components described herein, however, plate 61 and brackets 65 are merely optional, and may have any other suitable components, features, or configurations as desired.

Mounting member 70 of the present example comprises a flange 74 is configured to be secured to a ceiling or other structure. In the present example, mounting member 70 is formed of metal, though any other suitable material or combinations may be used. Mounting member 70 may have any other suitable features, components, or configurations. By way of example only, mounting member 70 may be configured in accordance with the teachings of U.S. Non-Provisional patent application Ser. No. 12/203,960, entitled "Ceiling Fan with Angled Mounting," filed Sep. 4, 2008, the disclosure of which is incorporated by reference herein. For instance, the device described in that patent application may be secured to upper flange 74; or directly to gearbox 60 in lieu of having mounting member 70 as shown. Still other suitable structures, devices, and techniques for mounting fan 10 to a ceiling or other structure will be apparent to those of ordinary skill in the art in view of the teachings herein.

As noted above, and as shown in FIG. 2, gearbox 60 provides a drive output through hollow output shaft 100. Hollow output shaft 100 is coupled with hub mounting flange 36 by a plurality of fasteners, such that hub mounting flange 36 (and, consequently, hub 30) rotates unitarily with output shaft 100. Alternatively, any other suitable devices, features, or techniques may be used to secure output shaft 100 to hub mounting flange 36, including but not limited to welding. An upper bearing 104 and an upper seal 105 may be provided between output shaft 100 and the housing of gearbox 60, such that output shaft 100 may rotate freely relative to the housing of gearbox 60 without any lubricant loss from gearbox 60.

A stationary tube 110 is positioned coaxially within output shaft 100. While stationary tube 110 is shown as having a generally circular cross section, stationary tube 110 may have any other suitable shape. A gap 112 is provided between the outer wall of stationary tube 110 and the inner wall of output shaft 100, such that output shaft 100 may rotate freely about stationary tube 110 without causing rotation of stationary tube 110.

Stationary tube 110 defines a central opening 124, through which wires, cables, plumbing, etc. may be passed. As shown in FIG. 2, stationary tube 110 is substantially longer than output shaft 100. In particular, a lower end 126 of stationary tube 110 protrudes downwardly past hub mounting flange 36 and the lower plane defined by hub 30, and through a lower bearing 128. Lower end 126 of stationary tube 110 is threaded in this example, though such threading is not necessary. Exposed lower end 126 may be used to mount a variety of components. It should be understood that since stationary tube 110 does not rotate, and is instead rotationally fixed relative to rotating components of fan 10, anything mounted to lower end 126 will also not rotate in this example.

It should be understood from the foregoing that stationary tube 110 may provide both a non-rotating feature (e.g., lower end 126, etc.) for attaching a variety of accessories to a fan system (10) and a passage (e.g., opening 124, etc.) through which electricity, further structural support, fluids, etc. may be provided to such accessories. Furthermore, output shaft 100, gearbox 60, hub 30, and associated components may provide rotation to drive fan blades 20 without substantially interfering with the above-noted aspects of stationary tube 110.

According to one aspect of the present disclosure, and turning to FIGS. 3-7, the fan 10 may be provided with one or more dynamic germicidal generators, such as in the form of ion generators 200 mounted to a movable portion of the fan 10, such as anywhere along one or more of the blades 20 (see FIG. 1). The dynamic mounting of the ion generator(s) 200 is advantageous in that such increases the number of ions generated (such as by the associated brushes 200a depending therefrom) and hence the efficacy of germicidal action. Indeed, in some one embodiment, the generator(s) 200 may be located adjacent to or at the radially outward end of the associated blade 20 (see, e.g., FIG. 1), where the airspeed is at a maximum or at least a higher value as compared to at the center of the fan 10. An exemplary ion generator 200 suitable for use is manufactured by Plasma Air International (Model: PA601, 12V DC) of Stamford, Conn., which device includes projecting brushes 200a that generate both positive and negative ions. This particular generator consumes little power, is lightweight and presents a low-profile so as to create a negligible impact on the operation of fan 10 in terms of generating air movement in an efficient manner.

Figure 4A:
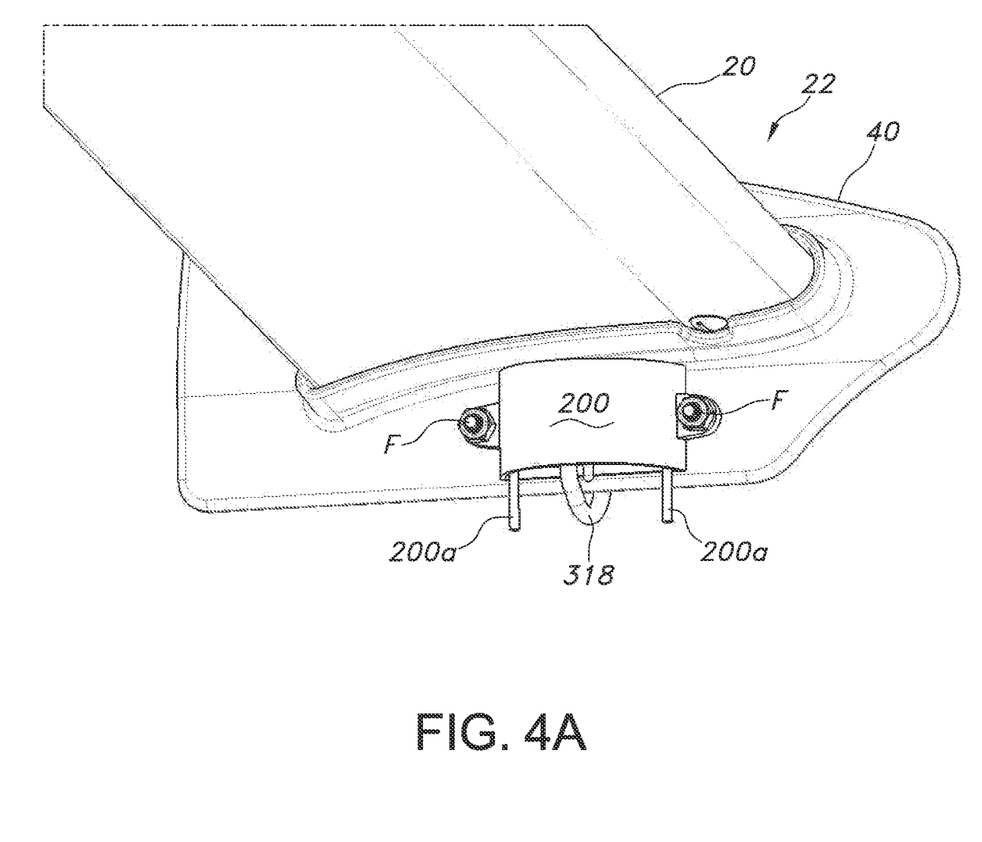

In one exemplary embodiment, the winglet 40 associated with the outer end 22 of each fan blade 20 carries the generator 200. The generator 200 may be connected anywhere along the winglet 40, such as for example on a depending portion and underneath the plane of the blade 20, as shown in FIGS. 4-4A. The connection of the generator 200 to the individual winglet 40 may be achieved using fasteners F, which may pass through the body of the winglet 40, as understood from viewing FIGS. 4, 4A, and 5.

Figure 6:
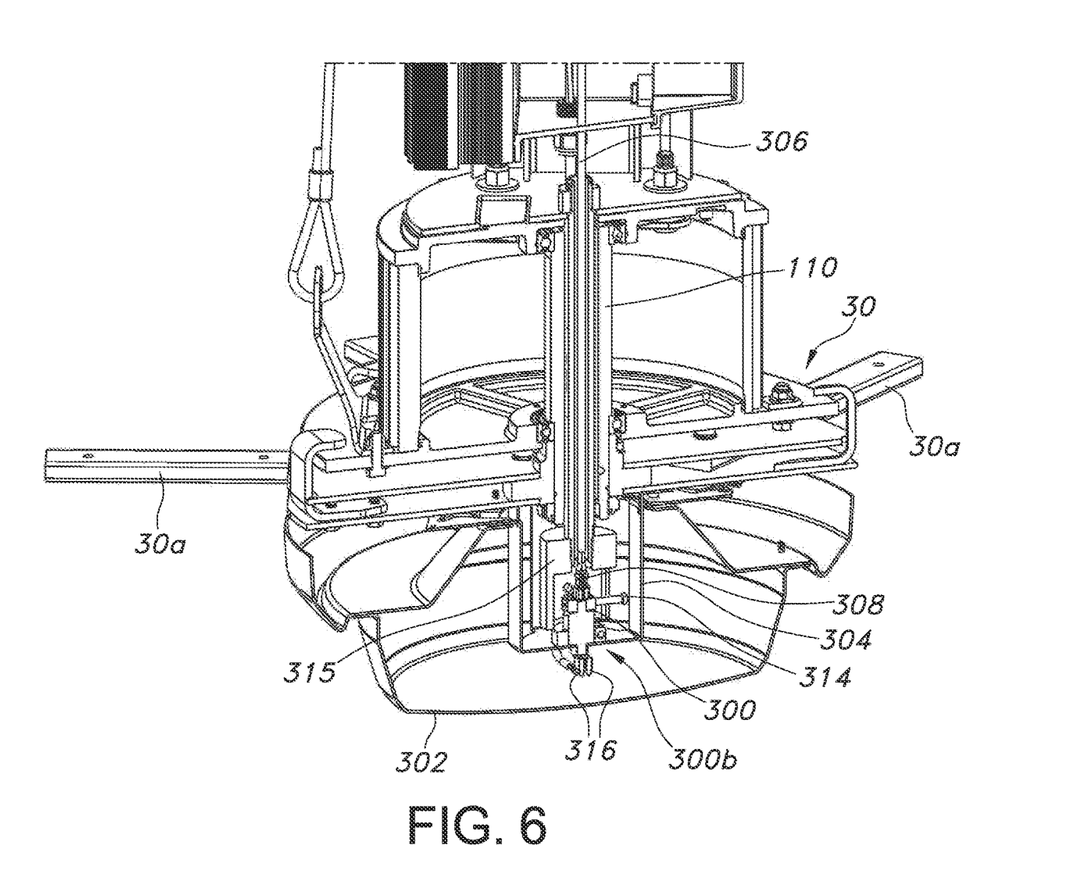
FIGS. 6 and 6A are partially cutaway, partially cross-sectional views of a fan including a rotary coupling for transmitting power to the fan blades.
Figure 6A:
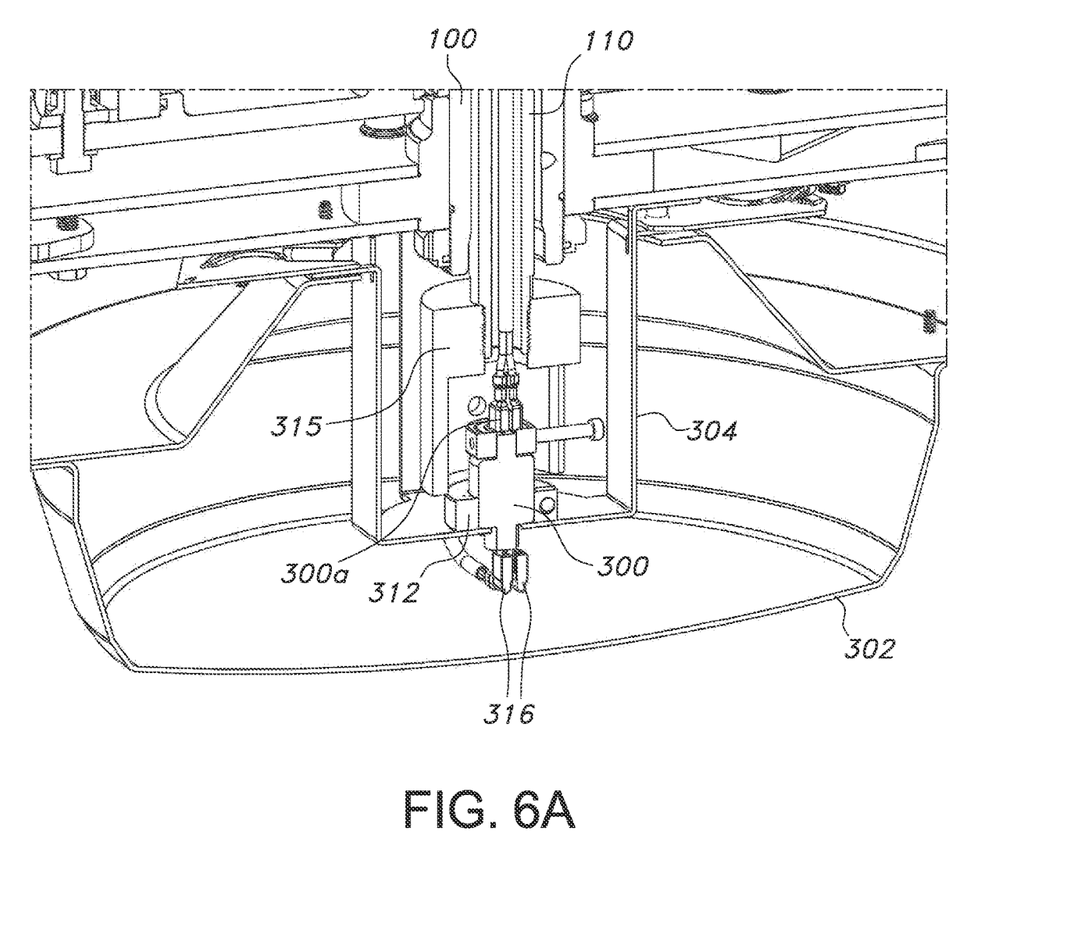
Figure 7:
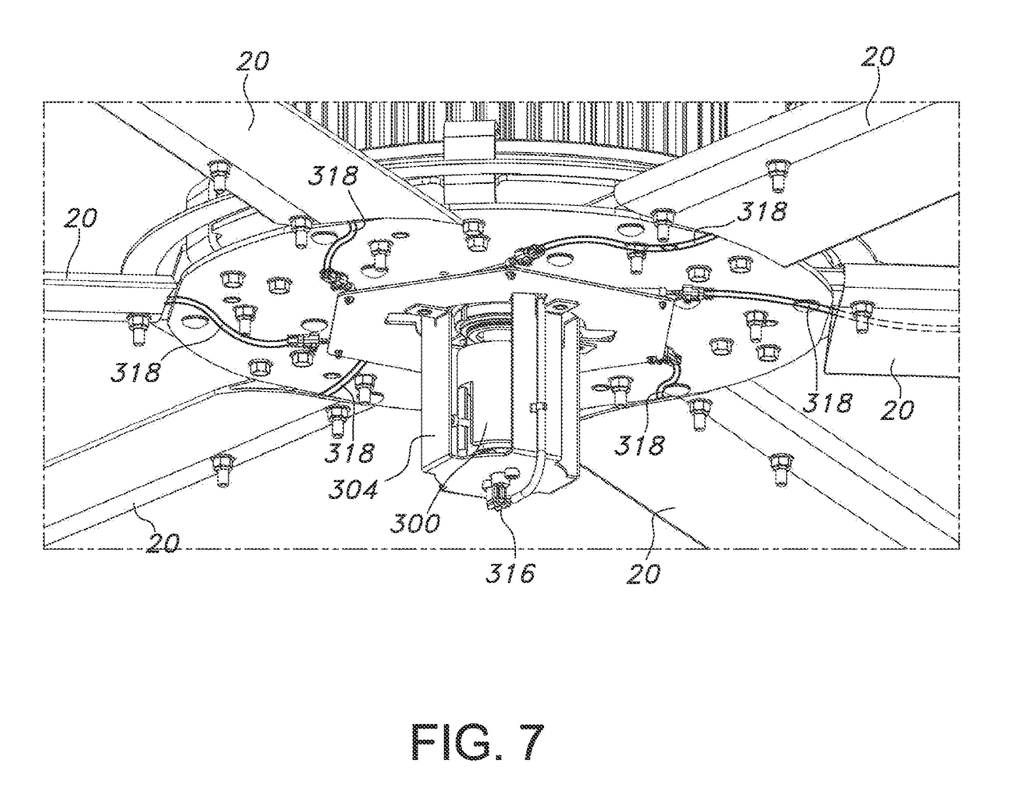
FIG. 7 is a partially cutaway bottom perspective view of a fan including a rotary coupling for transmitting power to the fan blades.
Figure 8:
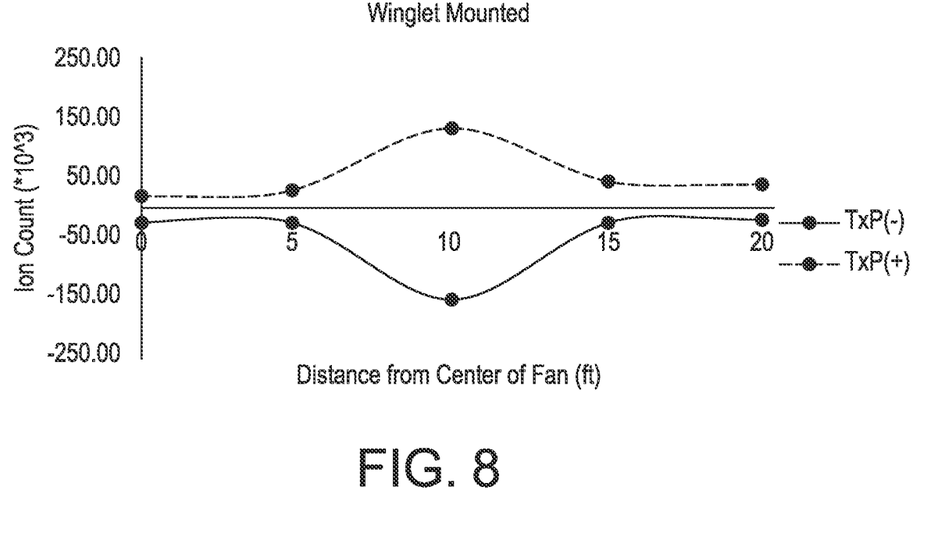
FIGS. 8-11 are graphical illustrations.
Figure 9:
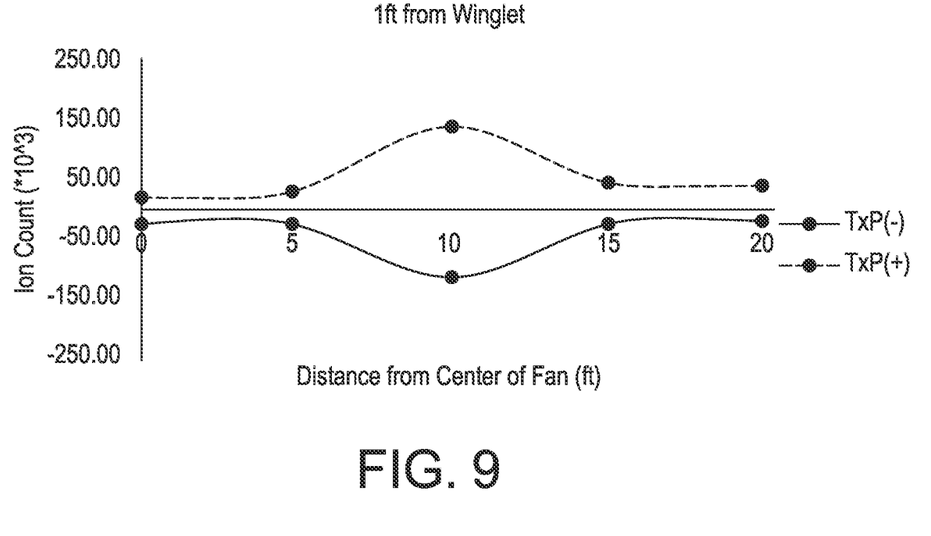
Figure 10:
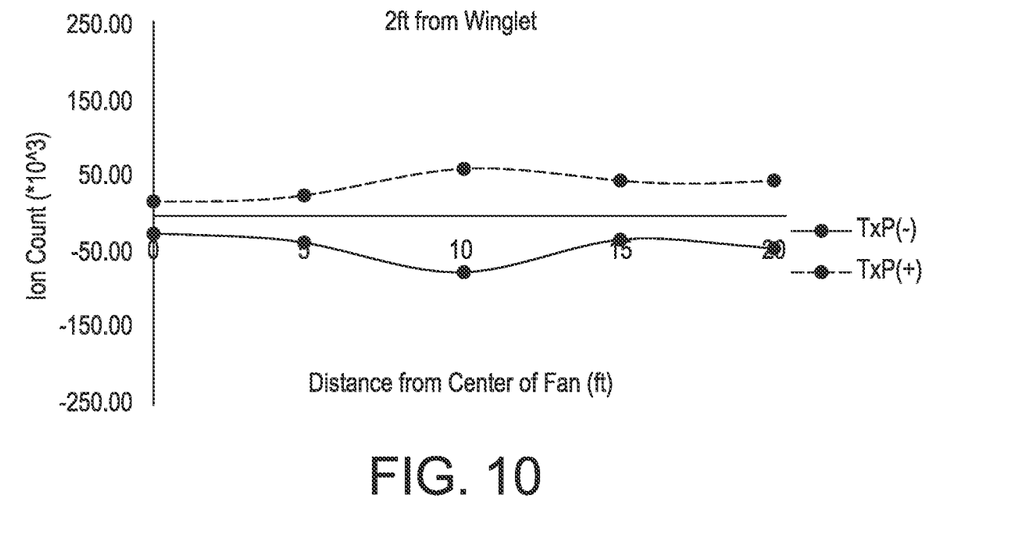
Figure 11:
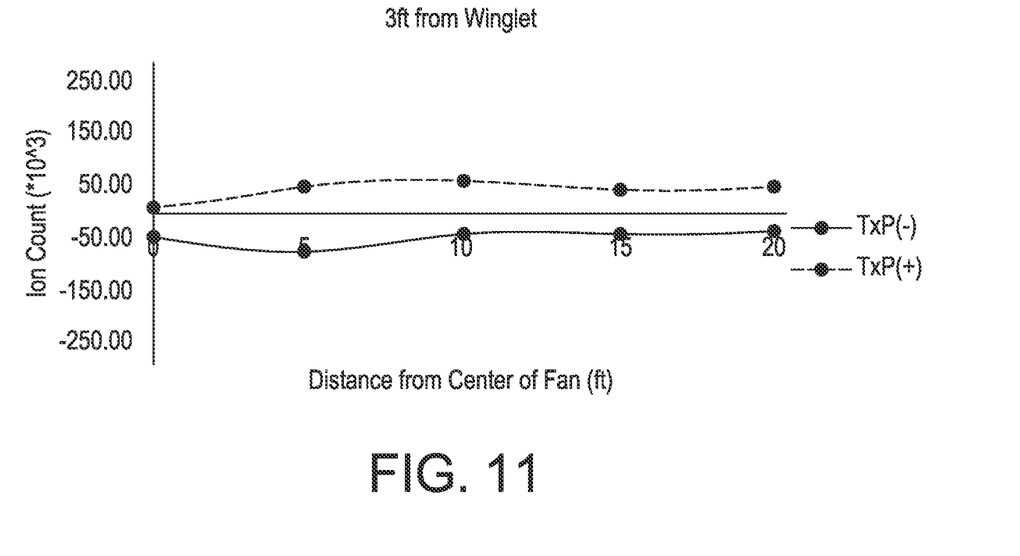

Power for the generator 200 may be supplied via a conduit including a dynamic rotary connector for transmitting power through a rotary coupling, such as a slip ring 300. Turning to FIGS. 6-7, the slip ring 300 may be mounted within a housing 302 supported by the stationary tube 110, such as by a depending support 304. The conduit further comprises a conduit or wires 306 for supplying power from a power source associated with the fan 10 to connectors 308 on the upper portion 300a of the slip ring 300, which is held stationary by a mount 312. A torque arm 314 may be provided for engaging a stop 315 mounted to the tube 110.

The lower portion 300b of the slip ring 300 includes connectors 316, which connect with individual pairs of wires 318 arranged in parallel for conveying power along the fan blade(s) 20 (such as through a channel formed by the hollow interior) to the associated ion generator 200, as can be seen in FIG. 7. Specifically, the wire pairs 318 may extend from a power supply associated with the fan through a channel in the hollow interior of the fan blade 20 to connect to the generator 200. The wire pairs 318 could also extend externally to the fan blade and be fastened (e.g., taped) to the exterior surface thereof.

Figure 5:
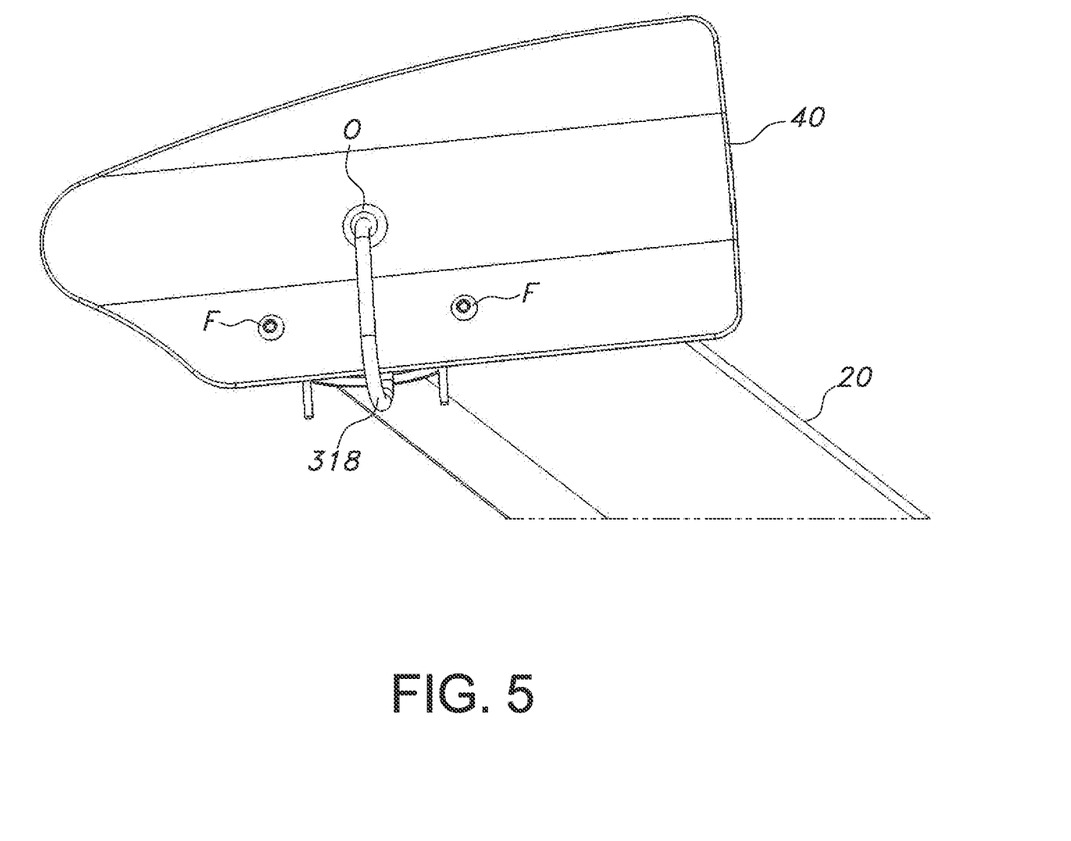
FIG. 5 is a partially cutaway view of an outer face of the winglet.

In the case where the generator 200 is mounted to the winglet 40 as shown, the wires 318 may pass through an opening O in the winglet 40 (see FIG. 5). Thus, when the fan 10 is actuated to cause hub 30 to rotate, the lower portion 300b of the slip ring 300 may also rotate while the upper portion 300a remains stationary. Nevertheless, the power connection and transmission remain continuous and hence dynamic ion generation occurs in a most efficient and effective manner as compared to a stationary source.

FIG. 1 illustrates an example where the generator 200 is carried by the fan blade 20, rather than the winglet 40 itself. In this case, electrical communication may be achieved by wires passing through or along the fan blade 20. In the case of interior passage of wires, the connection with the generator 200 may be made through an opening in the fan blade 20 suitable to allow for the wires to alight therefrom.

EXAMPLE

In order to test the efficacy of the proposed fan and also confirm optimal positioning of the germicidal generator, a test stand that locate and ion meter and air speed sensor are located 43 inches above the floor. Testing was completed for four different ion generator positions along the length of a fan blade on a fan according to the disclosure, using multiple positions of the test stand from the center of the fan and different ion generator samples. The ion density and air speed were recorded at five locations for each position. The starting position was the center of the fan. Each additional point was a five-foot incremented point in a straight line from the center ending twenty feet from the center of the fan. These points were marked with tape on the floor for consistency, and the test stand was placed just behind the yellow tape marker on the ground for each test. For the purposes of the test, an area under and around the fan was cleared and cleaned so that nothing would interfere with the air flow or ion readings. The HVAC system was also set to off and the automatic fan setting was set to zero. Whenever possible the HVAC and fan were turned back on while the test configuration needed to be adjusted so that the room conditions would remain relatively similar. The test fan was set to 50% power and the resulting RPM was recorded to be 52.4. Prior to commencing testing, the fan was turned on for at least five minutes, which allowed the airflow in the room to settle before testing began.

Data was collected for the test including the positive and negative ion count at five different locations for each position on the winglet. This was recorded alongside the temperature and air flow at each location. At the start of each position a room temperature and relative humidity were recorded.

The test results were recorded with the base position listed as 0 which denotes how far from the distal or winglet end of the fan blade the generator is in feet. Position 1 which is listed in the data tables as 1 in order to represent that it is one foot from the end of the fan blade.

From the following table, it can be appreciated that the highest ion density values were achieved at or closest (0'-1') to the winglet at the end of the fan blade:

| Ion Density/Distance from Winglet | 0' | 1' | 2' | 3' |
|---|---|---|---|---|
| 0 (−) | −25.53 | −25.58 | −25.60 | −51.12 |
| 5 (−) | −28.97 | −23.44 | −38.47 | −77.74 |
| 10 (−) | −161.20 | −118.66 | −75.44 | −47.27 |
| 15 (−) | −30.88 | −24.33 | −32.96 | −44.66 |
| 20 (−) | −26.11 | −27.59 | −43.54 | −41.15 |
| 0 (+) | 18.20 | 20.74 | 20.17 | 5.25 |
| 5 (+) | 27.01 | 29.16 | 25.85 | 47.41 |
| 10 (+) | 132.34 | 146.97 | 61.78 | 56.43 |
| 15 (+) | 43.71 | 45.10 | 47.37 | 42.37 |
| 20 (+) | 37.73 | 40.87 | 46.48 | 47.19 |
| Temp (F.) | 73.73 | 71.92 | 72.48 | 73.22 |
| RH (%) | 45.20 | 45.00 | 45.20 | 45.00 |

The results are illustrated graphically in FIGS. 8-11, and demonstrate the optimal positioning of the ion generator 200 according to one aspect of the disclosure. However, as can be understood, ion generation was still achieved at other blade positions, and is believed to be adequate to provide a desirable level of germicidal capabilities to the fan. It should also be understood that the ion generators may be provided at a different position along each fan blade to vary the amount and field of ion generation.

Summarizing, this disclosure relates to the following items:

1. A fan for improving air quality, comprising:
   (a) a motor;
   (b) a rotatable hub coupled to the motor;
   (c) at least one fan blade comprising: i. a first end coupled to the rotatable hub, ii. a second end radially distant from the rotatable hub, and iii. a winglet attached to the second end; and
   (d) at least one ion generator carried by the winglet.

2. The fan of item 1, wherein the at least one ion generator is mounted to an inner face of the winglet.

3. The fan of item 1 or item 2, wherein the at least one ion generator is mounted to the winglet below a plane of the at least one fan blade.

4. The fan of any of items 1-3, further including a rotary coupling for transmitting power to the at least one ion generator.

5. The fan of claim 4, further including a stationary tube passing through the hub for conveying power to the at least one ion generator, the rotary coupling connected to the stationary tube.

6. The fan of any of items 1-5, wherein a conduit for supplying power for the ion generator passes from the hub, along the at least one fan blade, and to the winglet to connect to the at least one ion generator.

7. The fan of any of items 1-6, wherein the at least one blade includes a passage extending from the first end to the second end, the passage including wires for transmitting power to the at least one ion generator through the winglet.

8. The fan of any of items 1-7, further including a plurality of fan blades coupled to the rotatable hub, each having a winglet including an ion generator.

9. The fan of any of items 1-8, wherein the at least one fan blade has a length of greater than about six feet.

10. A fan for improving air quality, comprising:
    (a) a motor;
    (b) a rotatable hub coupled to the motor;
    (c) at least one fan blade comprising: i. a first end portion coupled to the rotatable hub, ii. a second end portion radially distant from the rotatable hub;
    (d) at least one ion generator carried by the fan blade, such as only at the second end portion; and
    (e) a rotary coupling for transmitting power to the at least one germicidal generator.

11. The fan of item 10, further including a winglet at the second end of the fan blade for carrying the at least one ion generator.

12. The fan of item 10 or item 11, wherein the at least one ion generator is mounted to an inner face of the winglet.

13. The fan of any of items 10-12, wherein the at least one ion generator is mounted to the winglet below a plane of the at least one fan blade.

14. The fan of any of items 10-13, wherein the fan blade is hollow, and further including a wire passing from the rotary coupling through the hollow fan blade to the at least one ion generator.

15. The fan of item 14, further including a stationary tube passing through the hub for conveying power to the at least one ion generator, the rotary coupling connected to the stationary tube.

16. The fan of any of items 10-15, wherein a conduit for supplying power passes from the hub, along the at least one fan blade, and to the at least one ion generator.

17. The fan of any of items 10-16, wherein the at least one blade includes a passage extending from the first end to the second end, the passage including wires for transmitting power to the at least one ion generator through the winglet.

18. The fan of any of items 10-17, further including a plurality of fan blades coupled to the rotatable hub, each having a winglet including an ion generator.

19. The fan of any of items 10-18, wherein the at least one fan blade has a length of greater than about six feet.

20. A fan for improving air quality, comprising:
    (a) a motor;
    (b) a rotatable hub coupled to the motor;
    (c) at least one fan blade comprising: i. a first end coupled to the rotatable hub, ii. a second end radially distant from the rotatable hub;
    (d) at least one ion generator for generating germicidal energy connected to the at least one fan blade; and
    (e) a stationary tube passing through the rotatable hub including a conduit for transmitting power; and
    (f) a rotary coupling for transmitting power from the conduit to the at least one ion generator.

21. The fan of item 20, further including a winglet at the second end of the fan blade for carrying the at least one germicidal generator.

22. The fan of item 20 or item 21, wherein the at least one ion generator is mounted to an inner face of the winglet.

23. The fan of any of items 20-21, wherein the at least one ion generator is mounted to the winglet below a plane of the at least one fan blade.

24. The fan of any of items 20-23, further including a stationary tube passing through the hub for conveying power to the at least one ion generator, the rotary coupling connected to the stationary tube.

25. The fan of any of items 20-24, wherein a conduit for supplying power for the at least one ion generator passes from the hub, along the at least one fan blade, and to the at least one ion generator.

26. The fan of any of items 20-25, wherein the at least one blade includes a passage extending from the first end to the second end, the passage including wires for transmitting power to the at least one ion generator through a portion of the at least one blade.

27. The fan of any of items 20-26, further including a plurality of fan blades coupled to the rotatable hub, each having a winglet including an ion generator.

28. The fan of any of items 20-27, wherein the at least one fan blade has a length of greater than about six feet.

29. A fan for improving air quality, comprising:
(a) a motor;
(b) a rotatable hub coupled to the motor;
(c) at least one hollow fan blade comprising: i. a first end portion coupled to the rotatable hub, ii. a second end portion radially distant from the rotatable hub;
(d) at least one ion generator carried by and external of the fan blade; and
(e) a wire extending to the at least one ion generator via the hollow fan blade.

30. The fan according to item 29, wherein the at least one ion generator is located at the second end portion of the fan blade.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

Each of the following terms written in singular grammatical form: "a", "an", and "the", as used herein, means "at least one", or "one or more". Use of the phrase "One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated components), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase "consisting essentially of." Each of the phrases "consisting of" and "consists of, as used herein, means "including and limited to". The phrase "consisting essentially of means that the stated entity or item (system, system unit, system sub-unit device, assembly, sub-assembly, mechanism, structure, component element or, peripheral equipment utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

Terms of approximation, such as the terms about, substantially, approximately, generally, etc., as used herein, refer to ±10% of the stated numerical value or as close as possible to a stated condition.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

The invention claimed is:

1. A fan for improving air quality, comprising:
(a) a motor;
(b) a rotatable hub coupled to the motor;
(c) at least one fan blade comprising: i. a first end portion coupled to the rotatable hub, and ii. a second end portion radially distant from the rotatable hub;
(d) at least one ion generator carried by the fan blade; and
(e) a rotary coupling for transmitting power to the at least one ion generator;
wherein the at least one fan blade is hollow, and further including a wire passing from the rotary coupling through the hollow fan blade to the at least one ion generator.

2. The fan of claim 1, further including a stationary tube passing through the hub for providing power to the at least one ion generator, the rotary coupling connected to a lower end of the stationary tube.

3. The fan of claim 1, wherein the wire passes from the rotary coupling into an opening of the first end portion of the hollow fan blade, along a passage within the at least one hollow fan blade, and to the at least one ion generator.

4. The fan of claim 1, wherein the at least one fan blade has a length of greater than about six feet.

5. The fan of claim 1, wherein the at least one fan blade comprises an airfoil shaped cross-section.

6. The fan of claim 1, wherein the at least one ion generator is mounted to a radially outermost portion of the at least one fan blade.

7. The fan of claim 1, wherein the at least one ion generator is located below the at least one fan blade.

8. A fan for improving air quality, comprising:
(a) a motor;
(b) a rotatable hub coupled to the motor;
(c) at least one fan blade comprising: i. a first end coupled to the rotatable hub, and ii. a second end radially distant from the rotatable hub;
(d) at least one ion generator for generating germicidal energy; and
(e) a stationary tube passing through the rotatable hub including a conduit for transmitting power; and
(f) a rotary coupling for transmitting power from the conduit to the at least one ion generator;
wherein the at least one blade includes a passage extending from the first end to the second end, the passage including wires for transmitting power to the at least one ion generator through a portion of the at least one blade.

9. The fan of claim 8, wherein the rotary coupling depends from the stationary tube.

10. The fan of claim 8, wherein the at least one fan blade has a length of greater than about six feet.

11. The fan of claim 8, wherein the at least one fan blade comprises an airfoil shaped cross-section.

12. The fan of claim 8, wherein the at least one ion generator is mounted to a radially outermost portion of the at least one fan blade.

13. The fan of claim 8, wherein the at least one ion generator is located below the at least one fan blade.

14. A fan for improving air quality, comprising:
(a) a motor;
(b) a rotatable hub coupled to the motor;
(c) at least one hollow fan blade comprising: i. a first end portion coupled to the rotatable hub, and ii. a second end portion radially distant from the rotatable hub;
(d) at least one ion generator carried external to the fan blade; and
(e) a wire extending to the at least one ion generator within a longitudinally extending passage of the hollow fan blade.

15. The fan according to claim 14, wherein the at least one ion generator is located at the second end portion of the fan blade.

16. The fan of claim 14, further including a rotary coupling for transmitting power to the at least one ion generator.

17. The fan of claim 14, further including a stationary tube passing through the hub for providing power to the at least one ion generator via a conduit, the rotary coupling connected to the stationary tube.

18. The fan of claim 14, wherein the passage extends from the first end portion to the second end portion, the passage including the wire for transmitting power to the at least one ion generator through the winglet.

19. The fan of claim 14, wherein the at least one fan blade has a length of greater than about six feet.

20. The fan of claim 14, wherein the at least one fan blade comprises an airfoil shaped cross-section.

21. The fan of claim 14, wherein the at least one ion generator is mounted to a radially outermost portion of the at least one fan blade.

22. The fan of claim 14, wherein the at least one ion generator is located below the at least one fan blade.

* * * * *